United States Patent
Sheridan et al.

(10) Patent No.: US 7,262,312 B2
(45) Date of Patent: Aug. 28, 2007

(54) PROCESS FOR PRODUCING ORGANOALKOXYSILANES FROM ORGANIC ACIDS OR CYANATES AND HALOALKYLALKOXYSILANES

(76) Inventors: Robert E. Sheridan, 200 Brandy Dr., Marietta, OH (US) 45750; Larry A. Divins, 297 Chichester La., Parkersburg, WV (US) 26104; Michael R. Powell, 367 Franklin St., New Martinsville, WV (US) 26155

( * ) Notice: Subject to any disclaimer, the term of this patent is extended or adjusted under 35 U.S.C. 154(b) by 145 days.

(21) Appl. No.: 11/238,208

(22) Filed: Sep. 29, 2005

(65) Prior Publication Data

US 2007/0032673 A1 Feb. 8, 2007

Related U.S. Application Data

(60) Provisional application No. 60/705,781, filed on Aug. 5, 2005.

(51) Int. Cl.
*C07F 7/04* (2006.01)

(52) U.S. Cl. .................. 556/414; 556/420; 556/440

(58) Field of Classification Search ............... 556/414, 556/420, 440
See application file for complete search history.

(56) References Cited

U.S. PATENT DOCUMENTS

| | | |
|---|---|---|
| 3,517,001 A | 6/1970 | Berger |
| 3,598,852 A | 8/1971 | Berger |
| 3,607,901 A | 9/1971 | Berger |
| 3,821,218 A | 6/1974 | Berger |
| 4,281,145 A | 7/1981 | Mitchell |
| 4,880,927 A | 11/1989 | Takago et al. |
| 4,946,977 A | 8/1990 | Bernhardt et al. |
| 5,132,423 A | 7/1992 | Brunelle et al. |
| 5,218,133 A | 6/1993 | Pepe et al. |
| 5,229,482 A | 7/1993 | Brunelle |
| 5,950,150 A | 9/1999 | Lloyd et al. |

FOREIGN PATENT DOCUMENTS

EP 483 480 8/1991

*Primary Examiner*—Samuel Barts

(57) ABSTRACT

A process for the preparation of organoalkoxysilanes containing one or more organic functional groups derived from organic acids or hydrogen cyanates, by a continuous or batch process utilizing a solid guanidinium salt as a phase transfer catalyst for the reaction between a liquid phase haloalkylalkoxysilane and a solid phase alkali or alkaline earth metal salt or ammonium salt of an organic acid or a metal cyanate.

29 Claims, No Drawings

PROCESS FOR PRODUCING ORGANOALKOXYSILANES FROM ORGANIC ACIDS OR CYANATES AND HALOALKYLALKOXYSILANES

CROSS REFERENCE TO RELATED APPLICATIONS

This application claims the benefit under 35 U.S.C. §119 (e) to Provisional Application No. 60/705,781 filed Aug. 5, 2005 and entitled "IMPROVED PROCESS FOR PRODUCING ORGANOALKOXYSILANES FROM ORGANIC ACIDS OR CYANATES AND HALOALKYLALKOXYSILANES," the contents of which are incorporated by reference herein.

BACKGROUND OF THE INVENTION

1. Field of the Invention

This invention relates to an improved process for the preparation of organoalkoxysilanes, which contain organic functional groups derived from organic acids or hydrogen cyanate. The process is based on the known reaction of alkali or alkaline earth metal salts or ammonium salts of organic acids or metal cyanates with haloalkylalkoxysilanes in the presence of phase transfer catalysts.

2. Description of Related Art

The use of guanidinium salt as a phase transfer catalyst for the preparation of organoalkoxysilanes from salts of organic acids and haloalkylalkoxysilanes is known. In particular, U.S. Pat. No. 5,950,150 to Simonian et al. discloses this phase transfer catalyst and its use in certain reactions related to producing isocyanurate and carboxylate silanes. U.S. Pat. No. 5,950,150 discloses methods to minimize the increase in temperature from the evolution of heat from a batch reaction to produce organoalkoxysilanes from an alkali metal salt or ammonium salt of an organic acid or a metal cyanate, but does not disclose methods for practicing a continuous or batch reaction or methods to produce the organoalkoxysilane product from the base organic acids or hydrogen cyanate.

Furthermore, U.S. Pat. No. 5,950,150 does not disclose that the preferred embodiment of the phase transfer catalyst, hexaethylguanidinium chloride, is commercially available only as an aqueous solution or dissolved in chlorobenzene or dichlorobenzene solvent. Either the aqueous or solvent form of the catalyst present substantial hindrances to the successful practicing of the process. Water reacts with the haloalkylalkoxysilane reactant and/or the organoalkoxysilane product to form by-product siloxanes, which decrease product yield. Additionally, the alcohol formed by the water hydrolysis reaction deactivates the guanidinium catalyst, which stops the reaction to form the organoalkoxysilane product. Chlorobenzene and dichlorobenzene are considered hazardous to humans since they are suspected carcinogens, moderately toxic, strong central nervous system depressants, and experimental teratogens. If introduced into a continuous or batch process with the phase transfer catalyst, chlorobenzene or dichlorobenzene would either enter into a distillation light ends recycle loop or become a waste stream. If the chlorobenzene or dichlorobenzene enters a continuous lights ends recycle loop, it will build to a high concentration and would have to be diverted to a waste stream. Either way, chlorobenzene or dichlorobenzene would become an undesired hazardous waste from the process.

The use of tetraalkylammonium and hexaalkylguanidinium salts as phase transfer catalysts in the preparation of various polymers is known. In particular, U.S. Pat. No. 5,132,423 discloses the reaction of bisphenol salts with halo- or nitro-substituted phthalimides in an organic medium to produce bisimides which, upon conversion to dianhydrides and reaction with diamines, form polyetherimides. U.S. Pat. No. 5,229,482 discloses a similar phase transfer catalyst reaction of bisphenol salts with halo- or nitro-substituted bis(phthalimido) derivatives of aromatic diamines or with similar compounds, resulting in the direct formation of polyetherimides and other polyether polymers. The phase transfer catalysts employed according to U.S. Pat. Nos. 5,132,423 and 5,229,482 are guanidinium salts and especially hexaalkylguanidinium salts.

There are four general methods for the synthesis of an organoalkoxysilane compound:

1. Hydrosilylation of allyl- or vinyl-functional compound with trialkoxysilane.
2. Hydrosilylation of allyl- or vinyl-functional compound with trichlorosilane and subsequent alcoholysis.
3. Reaction of chloropropyltrimethoxysilane with a sodium or potassium salt of organic acid.
4. Reaction of an aminoalkysilane with a carbonate to form the product via the carbamate.

U.S. Pat. No. 3,517,001 discloses the first method and cites that isocyanurate-organosilanes have been prepared in the past by adding hydrosilanes to unsaturated isocyanates and more specifically allyl isocyanate in the presence of metal catalysts. This process is limited on a large scale because the hydrosilanes are expensive and the unsaturated isocyanates are typically highly toxic.

The first method suffers from many practical problems such as a slow hydrosilylation process, formation of by-products containing internal olefins, use of toxic and low flash point reagents such as trimethoxy- or triethoxysilane.

The second method is described in U.S. Pat. No. 4,281,145. It teaches that bis(3-trimethylsilylpropyl) fumarate can be made by the hydrosilylation of diallyl maleate with trichlorosilane and subsequent methoxylation of the trichlorosilyl compound to the desired product. Unfortunately, the handling of trichlorosilane is very dangerous due to the low boiling point, very high reactivity and toxicity of this material. Also the methanolysis process is difficult to control and produces large amounts of waste.

The third method is described in U.S. Pat. Nos. 3,607,901; 3,821,218, and 3,598,852. These methods are for synthesizing 1,3,5-tris(trialkoxysilylpropyl) isocyanurates. This process involves the reaction of potassium cyanate with chloropropylmethoxysilane in a polar aprotic solvent such as N,N dimethylformamide (DMF) which is toxic and difficult to remove. The reaction time is about 3 to 8 hours. The resulting material has purity about 70% and is highly colored.

Patents such as U.S. Pat. No. 5,218,133 and U.S. Pat. No. 4,880,927 disclose the fourth method and disclose that aminoalkylsilanes can be reacted with carbonates such as dimethyl carbonate in basic conditions which will form the carbamate. The carbamate is then neutralized and converted to the isocyanurate by a lengthy, high temperature, subatmospheric pressure cracking reaction which necessitates the use of a cracking catalyst such as aluminum triethoxide and a base catalyst such as sodium acetate.

U.S. Pat. No. 4,946,977 discloses the preparation of methacryloxypropyltrimethoxysilane by contacting potassium methacrylate with chloropropyltrimethoxysilane in the presence of tetraalkylammonium halides as phase transfer catalyst. The yield of the reaction is below 90% and the resulting product usually has a dark color due the thermal decomposition of the catalyst.

European patent application 483,480 describes the preparation of methacryloxypropyltrimethoxysilane with high yield by the contacting of potassium methacrylate with chloropropyltrimethoxysilane in the presence of 4-N,N-dialkylaminopyridine as a catalyst. 4-Dialkylaminopyridine is an effective catalyst in these processes but the use of dialkylaminopyridine is limited due to very high toxicity of these compounds.

It is therefore an object of the present invention to devise a continuous or batch process for performing the entire process for producing an organoalkoxysilane from an organic acid or a hydrogen cyanate and a haloalkylalkoxysilane. It is an object of this invention to provide a method for introducing commercial guanidinium salt as a phase transfer catalyst into the process without the generation of hazardous by-products. Furthermore, it is an object of this invention to provide a method for producing sulfur and phosphorus containing silanes and amide silanes in addition to the isocyanurate and carboxylate silanes of the prior art.

SUMMARY OF THE INVENTION

The present invention is a novel process for preparing an organoalkoxysilane from organic acids or hydrogen cyanate and haloalkylalkoxysilanes. Additionally it is an improved process for the utilization of a guanidinium salt as a phase transfer catalyst for the reactions of alkali or alkaline earth metal salts or ammonium salts of organic acids or metal cyanates with haloalkylalkoxysilanes. The guanidinium salts are used in the absence of chlorobenzene or dichlorobenzene. The method comprises:

a) reacting an organic acid or hydrogen cyanate with a base to form an alkali or alkaline earth metal salt or ammonium salt of the organic acid or metal cyanate in the wet or dry state, b) mixing the neutralized organic acid or metal cyanate in the wet or dry state with a catalytic amount of a guanidinium salt, c) producing a solid state mixture of the neutralized organic acid or metal cyanate and the guanidinium salt; and d) reacting the solid state mixture of the neutralized organic acid or metal cyanate and guanidinium salt with a liquid haloalkylalkoxysilane to provide organoalkoxysilane product and alkali metal halide or ammonium halide by-product.

DESCRIPTION OF THE INVENTION

It has been discovered, surprisingly, that organoalkoxysilanes, which contain organic functional groups derived from organic acids or hydrogen cyanates, can be manufactured simply and economically by a continuous or batch process utilizing a solid guanidinium salt as a phase transfer catalyst for the reaction between a liquid phase haloalkylalkoxysilane and a solid phase alkali or alkaline earth metal salt or ammonium salt of an organic acid or a metal cyanate. We discovered that guanidinium salt has solubility in haloalkylalkoxysilanes, which enables the solid phase guanidinium salt to perform as a phase transfer catalyst in this solid and single liquid phase system. Consequently, the process can be run neat without the use of solvents or optionally with solvents. The reactions are characterized by high yields and fast reaction times.

The first step in the process is the neutralization reaction of an organic acid or a hydrogen cyanate with a base to form a solution, slurry, paste, or solid form of an alkali or alkaline earth metal salt or ammonium salt of the organic acid or a metal cyanate. The base may be an alkali or alkaline earth metal, an alkali or basic salt of the metal, a metal alcoholate, or ammonia. The reaction is controlled to a near stoichiometric molar ratio and is cooled to remove the heat of reaction.

An especially preferred embodiment is the use of aqueous solutions of the alkali or basic salt of the alkali or alkaline earth metal or ammonia and guanidinium salt. In this embodiment, the reaction product form depends on the water content of the alkali or ammonium base. If a low water content base is used, the product is a paste. With a more dilute base, the reaction leads to a solution. If a solid base is used with a liquid organic acid, the product is a solid.

Suitable organic acids that may be utilized include, but are not limited to, carboxylic acids, dicarboxylic acids, phosphinic and phosphonic acids, sulfinic, sulfonic, and sulfamic acids, hydroxamic acids and the like, and mixture thereof. Accordingly, the carboxylic acids that may be utilized include, but are not limited to, acrylic, methacrylic, butenoic, butenedioic, and the like. Generally, both alkyl and aromatic forms of the organic acids may be utilized.

Suitable bases for use in the present invention may be an alkali or alkaline earth metal, an alkali or basic salt of the metal, a metal alcoholate, or an ammonia, and the metal cation is derived from the alkali metals of group 1A and the alkaline earth metals of group 2A of the periodic table. Suitable alkali or alkaline earth metal bases may include, but are not limited to, sodium, potassium, lithium, calcium, barium, rubidium, magnesium, and the like. The preferred bases of the present invention are sodium, potassium, lithium, magnesium and mixtures thereof. Most preferably, the bases of the present invention are derived from the alkali metals sodium and potassium.

According to another embodiment of the present invention, the base may be a metal alcoholate, such as, metal methylate or metal ethylate. Suitable metal alcoholates may include but are not limited to, sodium methylate, sodium ethylate, potassium methylate, potassium ethylate, magnesium methylate, magnesium ethylate, calcium methylate, calcium ethylate, and mixtures thereof. Most preferably, the metal alcoholates of the present invention are sodium methylate, sodium ethylate, potassium methylate, and potassium ethylate.

The next step in the preferred embodiment of the process is to mix aqueous guanidinium phase transfer catalyst solution with the solution, slurry, or paste from the first step at the required level of catalyst concentration needed for the product reaction step The guanidinium salts that may be employed herein have the following formula:

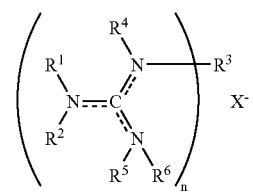

wherein $R^{1-2}$ and $R^{4-6}$ are independently selected from the group consisting of alkyl of 1–12 carbons preferably 2–6 carbons, cycloalkyl, phenyl; $R^3$ is alkyl or alkylene of 1–12 and preferably 2–6 carbons, or each $R^{1-2}$, $R^{3-4}$ and $R^{5-6}$ pair together with N attached thereto is piperidino or pyrrolidino or morpholino; $X^-$ is a halogen, boron fluoride (BF4), alkyl sulfonate, hydrogen sulfate, sulfates or carboxylates; and n is 1 or 2. Preferably, the guanidinium salt is a phase transfer catalyst having an hexaallkylguanidinium moiety wherein the alkyl is an aliphatic hydrocarbon radical having up to 40 carbons atoms such as hexaethylguanidinium, hexabutylguanidinium, and tetraethyldibutylguanidinium, and the like, and mixtures thereof. More particularly the guanidinium salt catalyst of this invention may be any of the guanidinium salts of the above formula containing about 12–30 carbon atoms. The guanidinium catalysts such as hexaethylguanidinium halide are significantly less toxic than other catalyst such as 4-(N,N-dimethylamino)pyridine and further have better thermal stability.

Drying the combined mixture of neutralized organic acid or metal cyanate and the guanidinium phase transfer catalyst to a solid is necessary before the next reaction step of the preferred embodiment. Residual water or alcohol content in the powder or solid is critical to the overall product yield since water generates siloxanes in the product reaction and alcohol inactivates the phase transfer catalyst. The dried solid must be maintained under a dry atmosphere to prevent moisture pickup by the hygroscopic guanidinium salt.

In an alternative embodiment of the present invention, if the base used in the neutralization reaction of the first step is a metal alcoholate, the drying or removal of alcohol and water from the alkali metal salt of organic acids or metal cyanates and the guanidinium halide phase transfer catalyst may be conducted before or after (in-situ) mixing with the haloalkylalkoxysilane for the product reaction step. The preferred embodiment is to dry the mixture before the product reaction step.

The product reaction step is the reaction of solid state alkali or alkaline earth metal or ammonium salt of the organic acid or metal cyanate and guanidinium phase transfer catalyst with liquid haloalkylalkoxysilane to form the desired organoalkoxysilane. The reactants are generally used at a stoichiometric ratio. A small excess of either reactant may be used if it is desired to fully consume one of the reactants. If the haloalkylalkoxysilane is additionally being utilized as a solvent for the purposes of washing product from the by-product salt, it may be advantageous to use excess haloalkylalkoxysilane in the reaction to dilute the formed by-product salt and improve mixing. A conventional solvent, e.g. xylene, toluene, hexane, heptane, and the like, may be utilized for the same purpose. However, alcohols may not be utilized because they inactivate the guanidinium phase transfer catalyst. Generally it is preferred not to use a solvent because the solvent slows the reaction rate.

The haloalkylalkoxysilanes that may be used in the practice of this invention are described by the general formula:

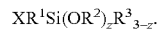

$XR^1Si(OR^2)_zR^3_{3-z}$.

Wherein $R^1$ is an alkyl, alkylene or alkylenoxyalkylene group comprising 1 to 20 carbon atoms. $R^2$ is an alkyl group comprising 1 to 4 carbon atoms or an alkoxyalkyl group comprising 2 to 4 carbon atoms. $R^3$ is a monovalent hydrocarbon group, and X is a halogen atom, and z is an integer of 1, 2, or 3.

The preferred haloalkylalkoxysilanes of the present invention are chloroalkylalkoxysilanes. Suitable chloroalkylalkoxysilanes of the present invention include, but not limited to, chloropropyltrimethoxysilane, chloropropyltriethoxysilane, chloropropylmethyldimethoxysilane, chloropropylmethyldiethoxysilane, chloropropyltris(methoxyethoxy)silane, chlorobutyltrimethoxysilane, chlorobutylmethyldimethoxysilane, chloromethyldimethylmethoxysilane, bromopropyltrimethoxysilane, and the like, and mixtures thereof. The most preferred chloroalkylalkoxysilanes of the present invention are chloropropyltrimethoxysilane, chloropropyltriethoxysilane, chloropropylmethyldimethoxysilane, and chloropropylmethyldiethoxysilane.

The guanidinium phase transfer catalyst is used in amounts of 0.001 mole to 0.1 mole, preferably in amounts of 0.003 mole to 0.03 mole, per molar equivalent of the alkali or alkaline earth metal salt or ammonium salt of the organic acid or metal cyanate content. The reaction temperature is in the range of about 80° C. to about 200° C., preferably about 100° C. to about 140° C. An advantage of the guanidinium phase transfer catalyst is its temperature stability throughout the reactor temperature range. Higher reactor temperatures than typical for other phase transfer catalysts may be utilized to speed the reaction rate and reduce reaction time. The reaction time is typically between 15 minutes and three hours.

If the alkali or alkaline earth metal salts originate from organic acids that may polymerize, e.g. the carboxylic acids with acrylate or methacrylate functionality, the product reaction composition may contain conventional polymerization inhibitors, which are suitable for the purpose. Examples of inhibitors of the present invention include, but not limited to, hydroquinone, hydroquinone monomethylether, 2,6-di-t-butyl-4methylphenol, 4,4'-methylenebis(2,6-di-t-butylphenol), phenothiazine, N,N-dialkylaminomethylene phenol, N,N'-diphenyl-p-phenylenediamine, phenyl-2-naphylamine, 2,2,6,6-tetramethyl(1-piperidinyloxy) radical, or a sulfur containing compound or combinations thereof. Generally these inhibitors are used in conjunction with a small amount of oxygen to maintain their activity.

Separation of by-product halide salt from the crude organoalkoxysilane product may be accomplished in two ways: one is by conventional mechanical means and the second is by water extraction. Conventional means may be filtration or centrifugation. If conventional separation methods are used, the filter or centrifuge cake should be washed to displace the organoalkoxysilane product. The haloalkylalkoxysilane reactant may serve this purpose or a compatible solvent may be utilized.

An optional method for by-product salt removal from the crude organoalkoxysilane product is by water extraction. Before conducting the water extraction, it is necessary to protect the crude product by adding a miscible solvent, e.g. xylene. The water extraction may be conducted by known batch or continuous methods. Preferably the water extraction is conducted with a water solution that is slightly basic in order to neutralize any acid halides or excess carboxylic acid in the crude product. The water phase will contain most of the guanidinium salt and will have to be treated for organics removal or decomposition before disposal.

Purification of the crude product is generally by vacuum distillation because of high boiling points. Although the crude product purity is good for many applications, excess haloalkylalkoxysilane or solvent from halide salt cake washing must be removed from the product. If the distillation involves organic groups that may polymerize, polymerization inhibitors are required.

A process to prepare the by-product halide salt for disposal or reuse is also contemplated herein. For economic and environmental reasons, the haloalkylalkoxysilane or solvent in the halide salt cake from filtration or centrifugation should be evaporated and recovered for reuse. It is also advantageous to hydrolyze any remaining trace haloalkylalkoxysilane or organoalkoxysilane product present in the halide salt after evaporation.

This invention is further disclosed by means of the following examples. It is understood, however, that the invention is not limited solely to the particular Examples given below. In the examples, all parts and percentages are by weight unless otherwise indicated.

COMPARATIVE EXAMPLES 1, 2, AND 4; EXAMPLES 3 AND 5–9

Comparative Example 1

This example was conducted without the use of polymerization inhibitors. To a 100 ml 4-neck round bottom flask fitted with a reflux condenser, thermocouple and magnetic stirrer was charged 4.98 grams (46 mmoles) of sodium methacrylate, 32.3 grams (163 mmoles) of chloropropyltrimethoxysilane and 0.10 grams (0.38 mmole) of hexaethylguanidinium chloride. The mixture was heated to 100° C. and held at that temperature for 3 hours. After this time the reaction mixture was cooled to room temperature and analyzed by gas chromatography. The crude reaction mixture was found to contain 29.2% methacryloxytrimethoxysilane. This represents an 88% yield based on the theoretical amount of contained product.

Comparative Example 2

This example was conducted with the use of polymerization inhibitors. To a 250 ml 4-neck round bottom flask fitted with a reflux condenser, thermocouple, and mechanical stirrer was charged 31.34 grams (290 mmole) of sodium methacrylate, 83.22 g (419 mmoles) chloropropyltrimethoxysilane, 0.04 grams of 2,6-di-t-butyl-4-methylphenol (BHT, 0.18 mmole), 0.12 grams of Ethanox 702®, and 6.0 grams of a 20% solution of hexaethylguanidinium chloride in o-dichlorobenzene (1.2 grams hexaethylguanidinium chloride, (4.5 mmole). This mixture was heated to 100° C. for 4 hours. After this time the resultant dark purple solution was analyzed by gas chromatography and found to contain 68.0% of methacryloxypropyltrimethoxysilane (98% of theory).

Example 3

A. Preparation of Sodium Methacrylate Solution

To a five liter 4-neck round bottom flask fitted with a reflux condenser, thermocouple, and mechanical stirrer was charged 1500.11 grams of de-ionized water. To this was incrementally added a total of 511.63 grams (12.79 moles) of sodium hydroxide pellets. The addition rate was such that the pot temperature did not exceed 50° C. After the solution cooled to room temperature, 1115.40 grams (12.82 moles) of methacrylic acid was added over the course of 2.5 hours. The temperature of the reaction mixture was kept below 50° C. throughout the methacrylic acid addition. This preparation resulted in a clear, colorless solution containing 44.1% by weight sodium methacrylate.

B. Addition of Hexaethylguanidinium Chloride and Co-Drying 426.17 grams of the sodium methacrylate solution prepared above was placed in a 32 oz wide mouth jar. To this was added 9.77 grams of a 34.5% aqueous solution of hexaethylguanidinium chloride (3.37 grams of hexaethylguanidinium chloride). The mouth of the jar was covered with aluminum foil and then placed in a vacuum oven. The oven was maintained at a temperature of 70° C. and a pressure of 125 mmHg overnight. After this time a slight nitrogen sweep was started to facilitate drying. The material was maintained at 90° C. and 125 mmHg until a constant weight was achieved. The dried powder is calculated to contain 1.76% by weight of the hexaethylguanidinium chloride.

C. Use of Co-Dried Sodium Methacrylate and Hexaethylguanidinium Chloride

To a 500 ml 4-neck round bottom flask fitted with a reflux condenser, thermocouple, and mechanical stirrer was charged 45.29 grams of the sodium methacrylate/hexaethylgaunidinium chloride prepared in the above preparation. This mixture contains 0.797 grams (3.02 mmoles) of hexaethylgaunidinium chloride and 44.49 grams (412 mmole) of sodium methacrylate. Also charged to the reaction vessel was 122.89 grams (618 mmole) of chloropropyltrimethoxysilane and 0.16 (0.37 mmole) of Ethanox 702®. This mixture was heated to 100° C. and held at that temperature for 5.5 hours. A sample of the crude reaction mixture contained 69.9 weight percent (98% of theory)methacryloxypropyltrimethoxysilane as determined by gas chromatography.

Comparative Example 4

This example illustrates the alternate preparation of methacryloxypropyltrimethoxysilane using a diluent solvent and water wash (extraction) to remove by-product sodium chloride salt from the crude product. To a 1000 ml 4-neck round bottom flask fitted with a reflux condenser, thermocouple, and mechanical stirrer was charged 153.21 grams (1.42 moles) of sodium methacrylate, 0.59 grams (1.4 mmoles) Ethanox 702®, 253.24 grams (1.27 moles) chloropropyltrimethoxysilane, and 112.33 grams of xylene. The mixture was heated to 100° C. At this temperature 38.66 grams of a 14.5% solution of hexaethylgaunidinium chloride in chlorobenzene was added. The reaction mixture was held at 100° C. for 5 hours. The resultant dark purple solution was then cooled to 50° C. and 257.5 grams of de-ionized water was added to the reaction vessel and stirred until the salt dissolved. The flask contents were poured into a 1-liter separatory funnel and the water layer removed. The organic portion was analyzed by gas chromatography and found to contain 63.7 weight percent methacryloxypropyltrimethoxysilane (94% of theory).

Example 5

This example illustrates the use of sodium methoxide as the neutralizing base. To a 500 ml 4-neck round bottom flask equipped with a reflux condenser, addition funnel, thermocouple and magnetic stirrer was charged 38.67 grams (0.45 moles) of methacrylic acid and 52.12 grams of methanol. To the addition funnel was charged 95.89 grams of a 25% solution of sodium methoxide in methanol (23.97 grams of contained sodium methoxide, 0.44 moles, 98.6% of theoretical). The sodium methoxide solution was slowly added to the methacrylic acid over a 1.3 hour period with vigorous stirring. Near the end of the addition the amount of formed solids made stirring difficult. After all of the sodium methoxide solution was charged, the addition funnel was rinsed with 17.53 grams of methanol. To the resulting thick slurry was added 3.21 grams of a 34% aqueous solution of hexaethylguanidinium chloride solution (1.09 grams of contained hexaethylguanidinium chloride, 4.1 mmoles). This material was rinsed into the reaction flask with 7.58 grams of methanol. The methanol was removed by mildly heating the reaction slurry under vacuum. The remaining paste was further dried by heating in a vacuum oven at 90° C. and 125 mmHg overnight.

The resulting dry solids were broken up with a spatula and the reaction flask fitted with a reflux condenser, thermocouple and mechanical stirrer. To the solids were added 0.192 grams (0.45 mmoles) of 4,4'-methylenebis(2,6-di-t-butylphenol), 0.081 grams (0.36 mmoles) of butylated hydroxytoluene (BHT) and 131.58 grams (0.66 moles) of chloropropyltrimethoxysilane. The mixture was then heated to 110° C. for 3 hours. During this time the color of the reaction mixture changes from purple to yellow. Analysis of the final product by gas chromatograpy indicated that the crude reaction mixture contained 72.3% of the desired gamma-methacryloxypropyltrimethoxysilane.

Example 6

This example illustrates the extension of the process of this invention to the production of acetoxyalkoxysilanes. In a 4-ounce glass jar was charged 20.23 grams (0.247 mole) of sodium acetate, 25.01 grams of deionized water, and 2.88 grams of a 34.5% aqueous solution of hexaethylguanidinium chloride (0.99 grams or 3.8 mmole of hexaethylguanidinium chloride). The mixture was loosely covered and placed in a vacuum oven at 110–120° C. and 125 mmHg for 72 hours to remove the water. To a 250 ml 4-neck round bottom flask fitted with a reflux condenser, thermocouple, and magnetic stir bar was charged 20.37 grams of the dried sodium acetate/hexaethylguanidinium chloride prepared above (19.42 grams or 0.237 mole of sodium acetate and 0.95 grams or 3.6 mmole of hexaethylguanidinium chloride) and 80.78 grams (0.41 mole) of 3-chloropropyltrimethoxysilane. The mixture was heated to 110° C. and held at this temperature for 7 hours. After this time the reaction was cooled to room temperature. Analysis of the crude reaction mixture by gas chromatography found that it contained 58.4% of 3-acetoxypropyltrimethoxysilane (96% of theoretical). The product identity was confirmed by GC/MS.

Example 7

This example illustrates the extension of the process of this invention to amides. To a 500 ml 4-neck round bottom flask fitted with a distillation head, mechanical stirrer, and thermocouple was charged 20.33 grams (0.34 moles) of acetamide and 111.5 grams of toluene. Water was azeotropically removed by slowly distilling out 25.7 grams of material from the pot. The remaining material was cooled to 56° C. and a total of 7.09 grams (0.31 moles) of metallic sodium was added in three increments over the course of an hour. Once all the sodium had been added the reaction mass was heated to 100° C. and held at that temperature for 3 hours. The mixture was then cooled to ambient temperature and 8.45 grams of a 14% solution of hexaethylguanidinium chloride in chlorobenzene was added (1.18 grams or 4.5 mmole of hexaethylguanidinium chloride). The toluene and chlorobenzene were then stripped off in vacuo at ambient temperature.

To the dry, brown residue produced above was added 91.49 grams (0.46 moles) of 3-chloropropyltrimethoxysilane. The pot contents were heated to 100° C. During the heat up, the reaction exothermed to 125° C. and required brief cooling in an ice bath. The reaction mass was held at 100° C. for 8 hours. After this time the pot contents were cooled to ambient temperature. The crude reaction mass was analyzed by gas chromatography and found to contain 24.8% of N-(propyl-trimethoxysilyl)acetamide (38% of theory). The product's identity was verified by GC/MS.

Example 8

This example illustrates the extension of the process of this invention to sulfur forms of organoalkoxysilanes. In a 4-ounce glass jar was added 10.13 grams (99.3 mmole) of sodium methyl sulfinic acid, 8.85 grams of deionized water, and 1.59 grams of a 34.5% aqueous solution of hexaethylguanidinium chloride (0.55 grams or 2.1 mmoles of hexaethylguanidinium chloride). The jar was loosely covered and placed in a vacuum oven at 110–120° C. and 125 mmHg overnight to remove the water. To a 500 ml 4-neck round bottom flask fitted with a reflux condenser, thermocouple, and magnetic stir bar was charged 10.71 grams of the dried mixture of sodium methyl sulfinic acid and hexaethylguanidinium chloride described above and 34.12 grams (172 mmole) of 3-chloropropyltrimethoxysilane. The mixture was heated to 110° C. and held at this temperature for 5 hours. After this time the reaction mass was cooled to room temperature. Analysis of the crude reaction mixture found it to contain 16.3% of the (propyltrimethoxysilyl)sulfinic acid ester and 34.6% of the (propyltrimethoxysilyl)methyl sulfone (combined content is 81.2% of theory). The identity of the products was confirmed by GC/MS.

Example 9

This example illustrates the extension of the process of this invention to produce phosphate forms of organoalkoxysilanes. To a 250 ml 3-neck round bottom flask fitted with a reflux condenser, thermocouple, and magnetic stir bar was charged 47.49 grams of xylene, 20.52 grams (82.0 mmole) of diphenyl phosphate, and 1.78 grams (77.4 mmole) of metallic sodium. The reaction was very slowly warmed. When the reaction mass reached approximately 30° C. it became difficult to stir. At this point 36.36 additional grams of xylene was added to help thin the reaction mass. At approximately 70° C. the diphenyl phosphate melts and becomes miscible in the xylenes. Between 90–100° C. the sodium melts and the reaction exotherms to 128° C. The reaction mass was cooled and held at 110° C. for 30 minutes and then cooled to room temperature. The resultant white solids were filtered through a 5 micron filter pad and washed twice with a total of 32.75 grams of xylene and blown dry. A total of 20.30 grams of dry solids were recovered (96% of theoretical). To a 50 ml round bottom flask was added 6.35 grams (23.3 mmole) of the sodium diphenyl phosphate whose preparation is described above. To this was added 1.05 grams of a 34.5% aqueous solution of hexaethylguanidinium chloride (0.362 grams or 1.4 mmole of hexaethylguanidinium chloride). The water was removed in vacuo. To a 250 ml 4-neck roundbottom flask fitted with a reflux condenser, thermocouple, and a magnetic stir bar was charged 6.64 grams of the dried mixture of sodium diphenyl phosphate and hexaethylguanidinium chloride described above (contains 6.28 grams or 23.1 mmole of sodium diphenyl phosphate and 0.36 grams or 1.4 mmole of hexaethylguanidinium chloride) and 38.36 grams (194 mmole) of 3-chloropropyltrimethoxysilane. The pot contents were heated to 120° C. and held at this temperature for 6 hours.

After this time the reaction was cooled to room temperature. Gas chromatographic analysis of the crude reaction product found 20.6% of the (propyltrimethoxysilyl ester of diphenyl phosphate (93.9% of theory). The structure of the product was confirmed by GC/MS.

Other embodiments of the invention will be apparent to those skilled in the art from a consideration of this specification or practice of the invention disclosed herein. It is intended that the specification and examples be considered as exemplary only, with the true scope and spirit of the invention being indicated by the following embodiments.

What is claimed is:

1. A process for preparing an organoalkoxysilane which comprises:
   a) reacting an organic acid or hydrogen cyanate with a base to form an alkali or alkaline earth metal salt or ammonium salt of the organic acid or metal cyanate in the wet or dry state,
   b) mixing the neutralized organic acid or metal cyanate in the wet or dry state with a catalytic amount of a guanidinium salt,
   c) producing a solid state mixture of the neutralized organic acid or metal cyanate and the guanidinium salt; and
   d) reacting the solid state mixture of the neutralized organic acid or metal cyanate and guanidinium salt with a liquid haloalkylalkoxysilane to provide organoalkoxysilane product and alkali metal halide or ammonium halide by-product.

2. The process of claim 1, wherein the haloalkylalkoxysilane is described by the general formula:

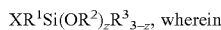

$XR^1Si(OR^2)_zR^3_{3-z}$, wherein $R^1$ is an alkyl, alkylene or alkylenoxyalkylene group comprising 1 to 20 carbon atoms;
$R^2$ is an alkyl group comprising 1 to 4 carbon atoms or an alkoxyalkyl group comprising 2 to 4 carbon atoms;
$R^3$ is a monovalent hydrocarbon group;
X is a halogen atom; and
z is an integer of 1, 2, or 3.

3. The process of claim 1, wherein the organic acid is selected from the group consisting of carboxylic, dicarboxylic, phosphinic, phosphonic, sulfinic, sulfonic, sulfamic, and hydroxamic acids.

4. The process of claim 1, wherein the guanidinium salt is a hexaalkylguanidinium salt.

5. The process of claim 4, wherein the alkyl group of the hexaalkylguanidinium salt is an aliphatic hydrocarbon of $C_1$–$C_{20}$ carbon atoms.

6. The process of claim 1, wherein the base is an alkali or alkaline earth metal, an alkali or basic salt of the metal, a metal alcoholate, or an ammonia and the metal cation is derived from the alkali metals of group 1A and the alkaline earth metals of group 2A of the periodic table.

7. The process of claim 1, wherein the base is an aqueous solution and neutralization reaction step (a) is conducted in an aqueous environment.

8. The process of claim 1, wherein the guanidinium salt is an aqueous solution.

9. The process of claim 6, wherein the metal alcoholate is metal methylate or metal ethylate.

10. The process of claim 1, wherein the neutralized organic acid or metal cyanate and guanidinium catalyst solutions are mixed with the haloalkylalkoxysilane before alcohol removal and drying.

11. The process of claim 1, wherein the carboxylic acid is selected from acrylic acid and methacrylic acid.

12. The process of claim 1, wherein the haloalkyalkoxysilane is a chloroalkylalkoxysilane.

13. The process of claim 12, wherein the chloroalkylalkoxysilane is selected from the group consisting of chloropropyltrimethoxysilane, chloropropyltriethoxysilane, chloropropylmethyldimethoxysilane, and chloropropylmethyldiethoxysilane.

14. The process of claim 1, wherein the molar ratio of the organic acid or hydrogen cyanate to the base is between about 1.2:1 and 1:1.2 per reactive site on the base.

15. The process of claim 1, wherein the molar ratio of the alkali or alkaline earth metal salt or ammonium salt of the organic acid or the metal cyanate to the haloalkylalkoxysilane is between about 1.2:1 and about 1:2 per reactive site on the alkali or alkaline earth metal salt or ammonium salt of the organic acid or the metal cyanate.

16. The process of claim 1, wherein the guanidinium salt is used in an amount of about 0.001 mole to about 0.1 mole per molar equivalent of the alkali or alkaline earth metal salt or ammonium salt of the organic acid or metal cyanate.

17. The process of claim 1, wherein the guanidinium salt is used in an amount of about 0.003 mole to about 0.03 mole per molar equivalent of the alkali or alkaline earth metal salt or ammonium salt of the organic acid or metal cyanate.

18. The process of claim 1, wherein the alkali metal salt of the organic acid or the metal cyanate is a salt or cyanate of sodium or potassium.

19. The process of claim 1, wherein the neutralization reaction step (a) is conducted at a temperature from about −50° C. to about 215° C. with simultaneous cooling to remove the heat of reaction, to form a solution, paste, or solid form of an alkali or alkaline earth metal salt or ammonium salt of the organic acid or metal cyanate.

20. The process of claim 1, wherein the product reaction step (d) is conducted at a temperature from about 80° C. to about 200° C., with sufficient residence time and with simultaneous cooling to remove the heat of reaction to form the crude organoalkoxysilane product and byproduct metal or ammonium halide salt.

21. The process of claim 1, wherein the reactions are performed in the absence of an added solvent.

22. The process of claim 1, wherein the haloalkylalkoxysilane is additionally utilized in excess as a diluent for the formed by-product halide salt and as a wash solvent for the separated by-product halide salt.

23. The process of claim 1, wherein a hydrocarbon solvent is utilized as a diluent for the formed by-product halide salt and/or as a wash solvent for the separated by-product halide salt.

24. The process of claim 23, wherein the hydrocarbon solvent is selected from the group consisting of toluene, xylene, hexane, heptane, an aliphatic mixture, and mixtures thereof.

25. The process of claim 1, wherein a hydrocarbon solvent is utilized to protect the organoalkoxysilane product during water extraction or separation of the by-product halide salt.

26. The process of claim 25, wherein the hydrocarbon solvent is selected from the group consisting of toluene, xylene, hexane, heptane, or an aliphatic mixture.

27. The process of claim 1, wherein polymerization is inhibited by the addition of one or more polymerization inhibitors.

28. The process of claim 27, wherein the polymerization inhibitor is selected from the group consisting of hydroquinone, hydroquinone monomethylether, 2,6-di-t-butyl-4-methylphenol, 4,4'-methylenebis(2,6-di-t-butylphenol), phenothiazine, N,N-dialkylaminomethylene phenol,N,N'-diphenyl-p-phenylenediamine, phenyl-2-naphylamine, 2,2,6,6-tetramethyl(1-piperidinyloxy) radical, or a sulfur containing compound or combinations thereof.

29. The process of claim 28, wherein the inhibitor is maintained active by the co-addition of oxygen.

* * * * *